US00PP08904P

United States Patent [19]

Drewlow

[11] Patent Number: Plant 8,904

[45] Date of Patent: Sep. 20, 1994

[54] IMPATIENS PLANT NAMED SHADOW

[75] Inventor: Lyndon W. Drewlow, Ashtabula, Ohio

[73] Assignee: Mikkelsens, Inc., Ashtabula, Ohio

[21] Appl. No.: 165,591

[22] Filed: Dec. 13, 1993

[51] Int. Cl.[5] ..... A01H 5/00
[52] U.S. Cl. ..... Plt./87.6
[58] Field of Search ..... Plt. 87.6

*Primary Examiner*—James R. Feyrer

*Attorney, Agent, or Firm*—Foley & Lardner

[57] ABSTRACT

A new and distinct cultivar of Impatiens plant named Shadow, characterized by its red-purple and purple-violet bicolor flowers, relative large diameter flowers, solid deep green leaves, early flowering habit, hightly self-branching and floriferous habits, flowering entirely above leaf canopy, tolerance to both high and cool temperatures, and its adaptability to be grown in 10 cm up to 15 to 25 cm containers.

1 Drawing Sheet

The present invention relates to a new and distinctive cultivar of Impatiens plant, botanically known as Impatiens, commercially known as New Guinea Impatiens, and known by the cultivar name Shadow.

The new cultivar was developed in a controlled breeding program conducted by the inventor Lyndon W. Drewlow in Ashtabula, Ohio. Shadow was created by crossing Mikkelsen Seedling No. 90-746-1 (seed parent) with Mikkelsen Seedling No. 90-254-2 (pollen parent). Both parents are proprietary cultivars used in the breeding program.

Asexual reproduction by terminal or stem cuttings carried out by or under the supervision of the inventor in Ashtabula, Ohio has shown that the unique features of Shadow are stabilized and are reproduced true to type in successive propagations.

The following combination of characteristics distinguish this new Impatiens from both its parent varieties and other cultivated Impatiens of this type known and used in the floricultural industry. Comparisons are made to the cultivar Sunregal, disclosed in U.S. Plant Pat. No. 6,389.

1. Shadow is a red purple (58B) and purple-violet (80C) bicolor while Sunregal is a red-purple (74B) and light red-purple (69A) bicolor.

2. Shadow has a flower diameter of 6.0 cm to 6.5 cm, compared to the smaller flower diameter of Sunregal of 5.0 to 5.5 cm.

3. Shadow has green stems with a reddish tint especially around nodes and areas near growing point on stems, while Sunregal has solid deep reddish-purple stems.

4. Flower spurs of Sunregal have dark green tips and a reddish coloration that covers about one-half to three-fourths of the spur. Shadow has reddish tips and a reddish tint that covers only the upper one-third to one-half of the spur.

5. Shadow has larger leaves, with the average mature leaf being 12 to 13 cm long and 3.0 to 3.5 cm wide. The smaller leaves of Sunregal are 9 to 10 cm long and 2.5 to 3.0 cm wide.

6. Shadow is 7 to 10 days earlier to bloom than Sunregal.

7. Shadow is a more upright growing plant with a plant height of 25 to 30 cm with dense branching, compared to Sunregal which is a more open plant with spreading habit and a plant height of 20 to 25 cm.

8. Flower pedicels of Shadow are 5.0 cm long resulting in the flowers being carried above leaf canopy, while Sunregal has 4.0 cm pedicels which results in more flowering in leaf canopy.

9. Shadow has 1 flower bud per leaf axil while Sunregal has 2 flower buds per leaf axil.

10. Sepals of Shadow are lighter red in color than Sunregal. The two secondary sepals of Shadow are 1.2 cm in length compared to the 1.0 cm long secondary sepals of Sunregal.

The accompanying color photograph comprises a top perspective view illustrating the overall appearance of Shadow, with the colors being as true as it is reasonably possible to obtain in a color reproduction of this type. The photograph was taken in Ashtabula, Ohio on Sep. 24, 1993 under natural light in a shaded glass greenhouse under 40% saran on a sunny day.

The following is a detaiuled description of Shadow based on plants produced in greenhouses in Ashtabula, Ohio during the summer season of the year. Plants were grown in 15 cm pots and measurements were taken 18 weeks after rooted cuttings were planted. Height measurements were taken from the soil line of the container. The plants were grown at 65°–68° F. night temperatures under 3000–4000 foot candles of light, and with 250 ppm nitrogen, 75 ppm potassium, and 250 ppm phosphorous nutritional levels, with trace elements added. Habit of growth, foliage coloration, leaf variegation, size of leaves and flower size will be influenced by nutritional and environmental conditions, without, however, any variation in genotype.

Color references are made to the Royal Horticultural Society Colour Chart except where general terms of ordinary dictionary significance are used.

Parentage: A controlled cross between female parent Mikkelsen Seedling No. 90-746-1 and male parent Mikkelsen Seedling No, 90-254-2.

Propagation:

(A) *Type cutting.*—Stem tip 15 mm long will develop 4 to 5 cm long in 18 to 21 days.

(B) *Time to root.*—8–10 days at 23° C. summer; 10–12 days at 20° C. winter.

(C) *Rooting habit.*—Heavy, fibrous.

Plant description:

(A) *Form and habit growth.*—Mounded to semi-upright, self-branched, intermediate in height, flowers open over top of leaf canopy; continuous flowering; vigorous growing flowering herb.

(B) *Foliage.*—Dark green with brownish-red cast, red-purple midrib and no leaf variegation. (1) Size: Average mature leaf is 13 cm to 14 cm long and 3.5 to 4.0 cm wide. (2) Shape: Lanceolate, with acuminate apex and acute base. (3) Texture: Both upper and lower surfaces are glabrous. (4) Margin: Finely serrated with fine ciliate. (5) Color: Young foliage, top side 147A with 183A cast, under side 183A; mature foliage, top side 147A with 183B cast, under side 183A. (6) Veination: pinnate, reddish purple in color.

Flowering description:

(A) *Flowering habits.*—Flowers continuously from leaf whorl of usually 6 to 7 leaves in a progressively orderly manner. There is usually one flower per leaf axil. When the last flower in the leaf whorl opens the first flower in the leaf whorl above starts to open. It takes 5 to 7 days for a mature bud to fully open, with the flower lasting two weeks or longer depending on the environment.

(B) *Natural flowering season.*—Indeterminant and continuous; quantity of flowering increases with increasing levels of light.

(C) *Flower buds.*—Ellipsoidal, flowers perfect; light green with reddish cast on upper one-third to one-half and reddish tip that is 5.0 cm on mature bud; the throat is behind the ovary and originates from the major sepal.

(D) *Flowers borne.*—On individual 5.0 cm yellow-green pedicels from a whorl of usually five (5) leaves, flowering progressively around the whorls as buds and leaves develop. Leaf axils have one flower each.

(E) *Quantity of flowers.*—Numerous because of highly self-branched nature of plant and long lasting flower characteristic.

(F) *Diameter of flower.*—6.0 to 6.5 cm.

(G) *Petals.*—(1) Shape: Heart; standard is largest petal. (2) Color: Top side in summer when opening is 58B and 80C bicolor, fading to 58C and 80D bicolor; under side is 58B and 80D bicolor. (3) Number of petals: Five (5) (4) Size of petals: Standard: 4.0 cm wide by 3.0 cm long, two equal lobes, shallow cut. Wings: 2.5 cm wide by 2.5 cm long, two unequal lobes, moderate cut. Keel: 3.25 cm wide by 3.0 cm long, two unequal lobes, deep cut.

(H) *Reproductive organs.*—(1) Stamens: Five (b 5) in number (a) Anther shape: hooded, color cream with reddish cast on hood. (b) Pollen color: white. (2) Pistels: (a) Stigma shape: Five (5) segmented column, color reddish-purple. (b) Style color: Reddish-purple. (c) Ovaries: Five (5) in number, size 5 mm mature, color dark green with reddish-purple cast.

Disease resistance: No significant disease or insect problems noted to date.

OTHER IMPORTANT CHARACTERISTICS

1. Self-branching early flowering habit of shadow allows cultivar to be grown in 10 cm pots, but Shadow is also vigorous enough to be grown in 15 to 25 cm containers as well.
2. Shadow has shown the ability to continue to bloom at both high temperatures and sunlight, as well as cool temperatures (40°–50° F.). Thus, the growing season outdoors of Shadow has been extended.

I claim:

1. A new and and distinct cultivar of Impatiens plant named Shadow, as illustrated and described.

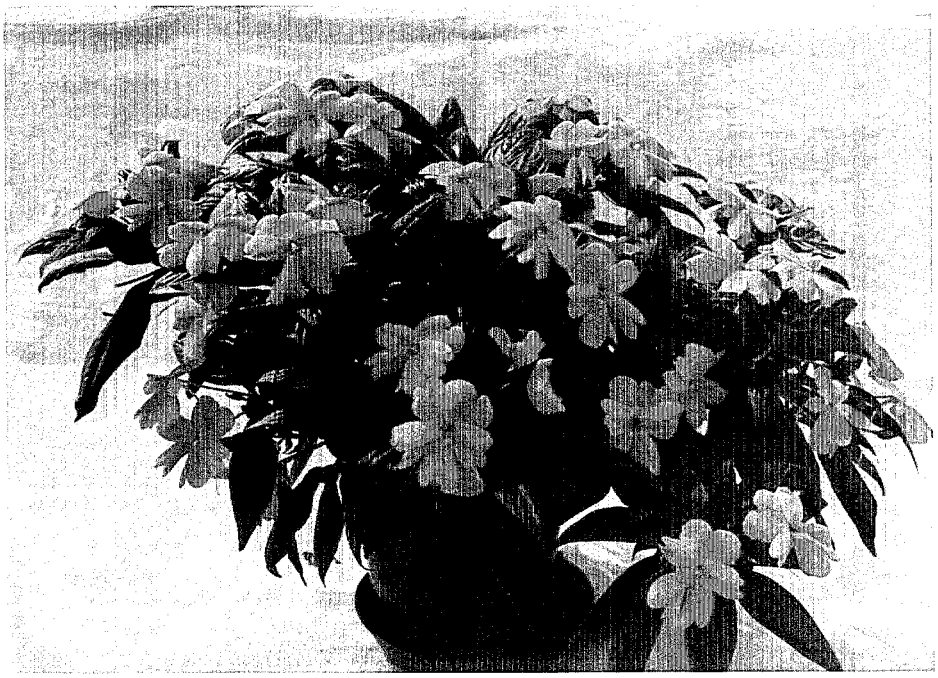

* * * * *